(12) United States Patent
Johansson et al.

(10) Patent No.: US 6,537,544 B1
(45) Date of Patent: Mar. 25, 2003

(54) FEED PRODUCT

(75) Inventors: Marie-Louise Johansson, Lund (SE); Clas Lönner, Eslöv (SE)

(73) Assignee: Probi AB, Lund (SE)

( * ) Notice: Subject to any disclaimer, the term of this patent is extended or adjusted under 35 U.S.C. 154(b) by 0 days.

(21) Appl. No.: 09/508,530

(22) PCT Filed: Oct. 5, 1998

(86) PCT No.: PCT/SE98/01796
§ 371 (c)(1),
(2), (4) Date: Jun. 20, 2000

(87) PCT Pub. No.: WO99/18188
PCT Pub. Date: Apr. 15, 1999

(30) Foreign Application Priority Data

Oct. 3, 1997 (SE) .............................................. 9703606

(51) Int. Cl.⁷ ................................................. C12N 1/00

(52) U.S. Cl. .................. 424/93.45; 424/93.1; 424/93.3; 424/93.4

(58) Field of Search ............................... 424/93.1, 93.3, 424/93.4, 93.45

(56) References Cited

U.S. PATENT DOCUMENTS 5,190,755 A   3/1993   Molin et al.
5,591,428 A   1/1997   Bengmark et al.

FOREIGN PATENT DOCUMENTS

WO   WO 93/01823   2/1993

*Primary Examiner*—Jean C. Witz
(74) *Attorney, Agent, or Firm*—Oblon, Spivak, McClelland, Maier & Neustadt, P.C.

(57) ABSTRACT

Novel strains *Lactobacillus plantarum* JI:1 and Lactobacillus species AC:3 are contained in an equine feed product. An oatmeal gruel fermented with said strains can be used for the prophylaxis or treatment of disturbances in the equine intestinal microflora, as well as gastritis.

14 Claims, 2 Drawing Sheets

FEED PRODUCT

The present invention refers to new strains of the genus Lactobacillus, and an equine feed product comprising one or more of said strains.

BACKGROUND OF THE INVENTION

Disturbances in the equine intestinal flora can bring about a deteriorated ability to take up the nutriment from the feed, a reduced efficiency, a deteriorated resistance to infections and accompanying infections of different kinds. Other symptoms are a changed consistency of the excrements, which are often malodorous, and an ugly coat of hair. It is well known that disturbances of the intestinal flora above all appear in stress situations, for instance during long transportations or change of stable environment, too tough training and change of feed, but also in treatment with antibiotics. Problems of a disturbed intestinal flora also occur in foals, which during their first living have to obtain an intestinal microflora of their own.

Different disorders which can be associated with a change of the intestinal bacterial flora are inflammations in the intestinal mucosa and gastric ulcer, and bacterial infections giving for instance acute colitis, such as intestinal chlostridiosis, manifesting in diarrhea and toxemia and caused by i.a. *Clostridium difficile*, and colic, such as Baron-Gruff-disease, which is caused by *Clostridium perfringens*.

The presence of coliform bacteria in the excrements has since long been used to judge the state of health in horses as to disturbances of the intestinal flora. A high content of said bacteria has been considered to indicate that the intestines are in good condition, while a low content thereof, as well as a high content of Bacillus and Clostridium spp, respectively, have been associated with intestinal disturbances. The presence of moulds and other fungus also have been considered to have an injurious effect on the intestinal flora. In addition a reduced body temperature, lower than 37° C., has been considered to indicate problems in the gastrointestinal tract. The normal temperature in horses is within the range 37.3–37.8° C.

Lactobacilli is one of the main groups of microorganisms in the intestinal microflora of healthy horses. Fujisawa et al. discloses in Bifidobacteria Microflora, Vol. 12(2), p. 87–90, 1993, the isolation of 286 strains of lactobacilli from the gastrointestinal tract of healthy horses. The main part of the strains could be identified as belonging to the species *L. salivarius*, *L. acidophilus* and *L. reuteri* and the last two species were found in all parts of the gastrointestinal tract while *L. salivarius* was not isolated from the stomach. It is also important to remember that the microflora is also influenced by the type of feed that the horse eats.

Probiotics, that is different bacterial and yeast preparations which are orally administrated with the purpose to improve the health in man and animals, have since long been used against intestinal disturbances to improve the intestinal function and the general state of health. As probiotics are commonly used different strains of lactic acid producing bacteria, such as strains of Lactobacillus and Streptococcus. The probiotic hypotesis says that if said bacteria can be added to the intestines in a sufficient amount during conditions of stress or illness, that is when the intestinal flora is disturbed in such a way that pathogenic bacteria are favoured, an establishment of the not wanted bacterial strains in the intestines will be counteracted. To maintain a healthy intestinal flora would then be decisive to prevent those disorders which are associated with a disturbance of the intestinal flora.

In Fox, Veterinary Medicine, August 1988, Probiotics: Intestinal inoculants for production animals, a review is made of different commercial probiotics used in raising different animals, especially chickens, pigs and calves.

PRIOR ART

It is today common to feed horses having malodorous excrements with sour milk or yoghurt to overcome the underlying disturbances in the stomach and intestines. Equine products on the market are for instance Bakteriebalans (Lantmännen, Sweden) and Lactosat® häst (Ewos Sverige AB, Södertälje) which both contain three different strains of lactic acid producing bacteria, that is of *Lactobacillus bulgaricus, Streptococcus thermophilus* and *Streptococcus faecium*. Said agents have in common that the lactobacilli which are present in the administrated products either are such which are naturally prevailing in the fermented product or such which have been isolated from man.

Another agent which has been used against equine intestinal disturbances is ColiCure (VETTECH AB, Stockholm), a product consisting of a purified and stabilized strain of *Eschericia coli*, which was originally isolated from horse, in a concentration of $>10^9$ viable bacteria/ml. The same principle is behind the administration of "mash", that is dispersed excrements from a healthy horse, that is to get a bacterial strain which fits into the intestinal environment and can become established therein. It is, however, controversial to add bacteria of the family Enterobacteriaceae, for instance *E. coli*, in view of pathogenicity and occurrence of endotoxines.

EP 0 203 586 discloses a composition for treatment of gastrointestinal disorders in animals, especially those being caused by enterotoxigenic strains of *Escherichia coli*, which is based on the strain *Lactobacillus fermentum* ATCC 53113, which has been isolated from pig. An advantage of the new composition is said to be that it is not pathogenic and acts by preventing infectious organisms from binding to the intestinal mucosa. An overview is also given of different bacteria which have been used to prevent or to remedy gastrointestinal disorders, but which have all turned out to be effective only in part.

It has previously been shown that certain strains of *Lactobacillus plantarum* have the ability for a certain period of time to become established in the intestinal system of man. In EP 92916294.9 certain strains of Lactobacillus, especially *L. plantarum* 299 DSM 6595 and variants thereof having the ability to become established in the intestines and to remain for at least 11 days after oral administration, are described. Said strains have turned out to have a favourable effect on different disturbances of the intestinal microflora in man.

The normal lactobacilli flora in the intestines of different animal species are different and although the same species of Lactobacillus can be found in two different animal species, the bacteria do not normally belong to the same strain of said species. The strains present differences between themselves which are of importance for their chances of becoming established in the actual environment. In order to be able to treat gastrointestinal disorders in horses, there is therefore a continous need of a safe, non-toxic product comprising one or more bacterial strains having the ability to become established in the equine intestines.

DESCRIPTION OF THE INVENTION

The invention refers to an equine feed product preventing and rectifying microbially caused intestinal disturbances, which contains one or more strains of Lactobacillus which have been isolated from the gastric or intestinal mucosa of horse and which have the ability to colonize in the equine intestines.

Horse refers in this connection to subjects of the genus Equidae, that is in addition to horse also donkey and zebra, having a similar composition of the intestinal flora.

The feed product according to the invention is preferably a feed which has been fermented with a strain of Lactobacillus which has been isolated from the gastric or intestinal mucosa of horse and which has the ability to colonize in the equine intestines.

The feed product according to the invention is preferably based on a cereal based grain or supplementary feed, green forage or hay.

A preferred aspect of the invention is a feed product based on oats which has been fermented with one or more strains of lactobacilli isolated from horse, especially with any of the new strains stated below.

According to another aspect of the invention the feed product is an ensilage based on green forage or hay which has been fermented with one or more strains of lactobacilli isolated from horse.

The invention also refers to the new strain *Lactobacillus plantarum* JI:1, which has been desposited with the Deutsche Sammlung von Mikroorganismen und Zellkulturen GmbH on Apr. 21, 1997, under number DSM 11520 and variants thereof; especially for use for prophylaxis or treatment of disturbances in the intestinal microflora.

The invention also refers to another new strain Lactobacillus species AC:3 and variants thereof, which has been deposited with the Deutsche Sammlung von Mikroorganismen und Zellkulturen GmbH on Oct. 2, 1998 under number DSM 12429.

The above strains have turned out to grow well on oats and give a tasty feed product, survive the passage through the gastrointestinal tract of the horse and have the ability to become established in the intestines of horse. Tests have shown that the new strain *Lactobacillus plantarum* JI:1 reduces the content of undesired bacteria in the equine intestines, for instance the total count of Bacillus and the total count of Clostridium and seems to improve the immune response of the horse.

The feed product according to the invention can be a supplementary feed or a feed, in solid or liquid form. The feed product can be a grain or supplementary feed based on any type of feed which can be fermented by the selected strains of lactobacilli, for instance cereals, such as oats, i.a. black oats, barley, wheat, rye, sorghum or corn, or vegetables, such as leguminous plants, especially soybeans, root vegetables and cabbage, or green forage, such as grass or hay.

Oats is a preferred feed owing to the high content of vitamins and minerals, the well-balanced amino acid composition, the contents of polar lipids and fibres. A variety of oats having a higher fat content has recently turned out to be an appropriate feed for high capacity horses.

A preferred aspect of a feed product according to the invention can be prepared from oats in accordance with the international patent application WO89/08405 referring to the preparation of a nutrient composition. Other examples of preparation of preferred feed products are given below.

The invention also refers to the use of one or more strains of Lactobacillus which have been isolated from the gastric or intestinal mucosa of horse having the ability to colonize in the equine intestines.

The invention also especially refers to the use of the new strain *Lactobacillus plantarum* JI:1 or a variant thereof for the prophylaxis or treatment of disturbances in the equine intestinal flora. Also inflammatory conditions in the gastric or intestinal mucosa can be alleviated. The invention especially refers to the use of said strain for the preparation of a product for prophylaxis or treatment of disturbances in the equine intestinal flora.

A feed product according to the invention can be administered before or in connection with stress situations, for instance during the warming up before a race, transportation etc. to horses which on occasions like those are stroken by diarrhea; to improve the common condition of horses which are thin, have a poor appetite or a bad coat; to make horses less sensitive to infections, that is to strengthen the immune response; during treatment with anti-biotics to prevent the disturbances of the intestinal flora which normally appear, and thus the diarrhea which is often associated with treatment with antibiotics; to horses having a gastric ulcer; to horses having a diarrhea or malodorous excrements which might be infected with *Clostridium difficile* or any other pathogenic microorganism.

The content of lactobacilli in the feed should not be below $5 \cdot 10^8$ CFU/g or ml and an adequate dose to grown up horses is $2.10^{12}$ CFU per day, which corresponds to about 2–4 litres of the oatmeal gruel exemplified below or about 100–200 ml of a freeze culture as below. Higher contents can without any risk be used on special occasions. When administrated to fouls a smaller amount should be given.

EXPERIMENTAL PART

Figure 1:
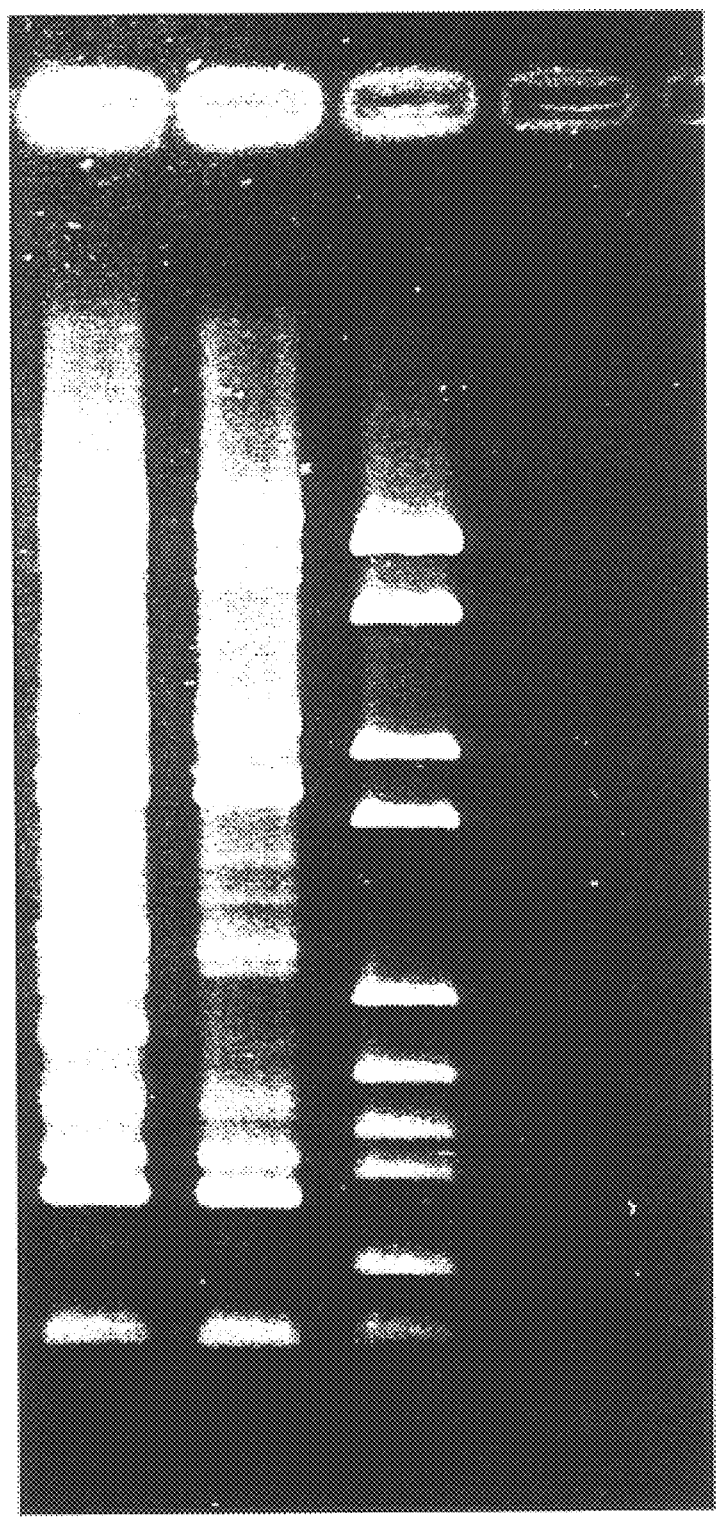
FIG. 1 shows a photography of an electrophoretic gel with strains which have been analysed by RAPD.

In order to produce the new strain representative strains of Lactobacillus have firstly been isolated from horse, said strains have then been classified and examined as to ability to ferment oats and rapidly give an adequate pH-reduction, good taste and smell, and finally feed experiments on horses have been done to evaluate the effect obtained.

Isolation of Strains of Lactobacilli

The lactobacilli flora in the gastrointestinal tract of 10 healthy, freshly slaughtered horses were investigated by taking biopsies of 1–2 cm² of the intestinal mucosa from three different places, that is the lower stomach (pylorus), the small intestine (ileum) and the large intestine (colon). The specimens were rinsed directly and carefully with sterile transport solution (0.9 g NaCl, 0.1 g peptone, 0.1 g Tween 80, 0.02 g cysteine per litre), in order to eliminate contamination from bacteria in the excrements, and were kept cool during the transportation to the laboratory. There the specimens were treated in an ultrasonic bath for 5 minutes and then in a tube shaker for 2 minutes, in order to loosen the bacteria from the intestinal mucosa. In total 51 samples were taken.

Identification of the Lactobacilli Flora in the Gastrointestinal Tract in Horse

From each sample 1 or 2 lactobacilli isolates were taken and characterized as to ability to ferment 49 different carbon sources according to the API 50 CH system (API Systems S.A., Montalieu, Vercieu, France). This normally gives species specific patterns and the results obtained were compared to the results of about 200 different, known strains of Lactobacillus comprising all type strains of all acknowledged species of lactobacilli. The following result was obtained:

| Species | % of the isolates |
|---|---|
| L. salivarius | 14 |
| L. salivarius-like | 29 |
| L. reuteri-like | 14 |
| L. johnsonii | 4 |
| L. johnsonii-like | 10 |
| L. plantarum | 12 |
| L. animalis | 6 |
| L. brevis | 2 |
| L. vaccinostercus-like | 2 |
| L. murinus | 2 |
| L. species | 4 |

Selected Strains and Characterizations

The isolated bacterial isolates were then investigated as to ability to ferment oatmeal gruel, which had been prepared as follows.

18.5% by weight oatmeal (MP-450, Kungsörnen AB, Järna) 0.925% by weight malted barley meal (MBF, Nord Malt AB, Sbderhamn) were mixed with tap water and heated to 95° C. while slowly stirred. After 30 minutes the gruel was cooled to 37° C. and fermented with the different strains for 20 h to a pH below 4. Especially the rate of reduction of the pH and the smell and aroma of the final product were investigated. The best results were obtained when using the isolate L. plantarum and L. salivarius-like as a starter culture and the worst results were obtained with L. reuteri and L. johnsonii-like.

Two strains were selected based on the above. The strains were identified phenotypically on API 50 CH and genotypically by means of the analysis methods RAPD and REA as Lactobacillus plantarum JI:1 and Lactobacillus species AC:3, respectively. In this process purified isolates were cultured over night in broth. Before inoculation in API 50 CHL medium the cultures were washed once in 0.9% NaCl-solution. The samples were read after 2 d and 7 d. The results were evaluated from 0 (violet) to 5 (yellow) and a value of 3–5 was regarded as positive.

Genotype Characterization

Randomly Amplified Polymorphic DNA (RAPD)

RAPD is a polymerase chain reaction (PCR) consisting of repeated cycles of template denaturation, primer annealing and primer extension. This will give an amplification of certain fragments of the genome.

Purified bacterial isolates were cultured over night in Lactobacillus Carrying Medium (LMC, Efthymiou and Hansen, 1992) with 1% glucose. Cells from 100 µl of the culture were recovered by centrifugation and washed twice in 1 ml sterile distilled water. The cells were resuspended in 0.25 ml sterile distilled water and then disintegrated by vigorous shaking with glass beads (diameter 0.2 mm) using an IKAVibrax VXR shaker (IKA Labortechnik Staufen, Germany) at the maximum speed for 30 minutes in the cold. The cell debris were pelleted by centrifugation and 1 µl of the supernatant was used for PCR. PCR was performed in a DNA Thermal Cycler 480 (Perkin Elmer, Norwalk, US) using a 9-mer primer (ACGCGCCCT; Pharmacia Biotech, Sweden) in a concentration of 8 µmol/l. The nucleotides were added at a concentration of 0.2 mmol/l of each dNTP (Perkin Elmer; Branchburg, N.J., US). The Taq-polymerase concentration was 50 U/ml (Boehringer Mannheim) and the buffer concentration was 100 U/ml (10×PCR buffer; Boehringer Mannheim). The reaction mixture was covered with mineral oil and subjected to the following temperature cycles: 94° C., 45 s; 30° C., 120 s; 72° C., 60 s during four cycles and then to 94° C., 45 s; 36° C., 30 s; 72° C., 30 s for 26 cycles (the extension step is made 1 s longer for each new cycle). The PCR process was completed at 75° C. for 10 min and the sample was then cooled to 4° C.

Gel electrophoresis was performed by adding 20 µl of the sample to a submerse, horizontal agarose gel plate consisting of 75 ml 1.5% agarose (type III: High EEO, Sigma, St. Louis, US) of a size of 150×115 mm. Gels were run for about 2.5 hours at 100 V in TB electrophoretic buffer (89 mM boric acid, 89 mM Tris-OH, 2.5 mM EDTA, pH 8.3) without cooling. 0.5 µm of a DNA molecular weight marker VI (Boehringer Mannheim Scandinavia, Bromma, Sweden), was used as a standard. After electrophoresis the gels were stained in ethidium bromide (3 µg ml$^{-1}$) for 5 minutes and then washed for 10 minutes and made visible at 302 nm with a UV transilluminator (UVP Inc., San Gabriel, Calif., US) and photographed.

In FIG. 1 the RAPD-pattern of, from the left, L. plantarum JI:1, the type strain of L. plantarum ATCC 149 17$^T$ and the marker are shown. From this can be seen that the pattern of this new strain according to the invention is slightly different from the pattern of the type strain. In the same way the proposed strain Lactobacillus salivarius-like AC:3 (according to API) differed from the type strain of L. salivarius ssp. salivarium ATCC 11741 (data not shown).

Purification of Chromosomal DNA

Preparation and purification of chromosomal DNA were performed according to the method described by Stahl et al., International Journal of Systematic Bacteriology 40:189–193, 1990. The strain were cultivated over night at 37° C. in 100 ml broth with 1% glucose and were then harvested and washed in TES (50 mM NaCl, 100 mM Tris, 70 mM sodium EDTA, pH 8.0) and suspended in 3 ml TES+25% (weight/volume) sucrose. 2 ml TES+25% sucrose supplemented with 120 mg lysozyme (quality VI, Sigma) and 140 U mutanolysine (Sigma) were added. The cells were incubated at 42° C. for 2 h; 3 mg proteinase K (quality XI; Sigma) were then added and the suspension was further incubated at 37° C. for 30 minutes. After cooling on ice 1 ml of a 5% NaCl solution was added, 1 ml 20% dodecyl sulphate and 11 ml TES and the suspension was carefully stirred with a glass bar and heated to 65° C. The cell lysate was then extracted once with redestilled phenol-chloroform (1:1) and once with isoamyl alcohol-chloroform (1:24). DNA was then precipitated with ethanol at 20° C.

The chromosomal DNA was then purified and separated from the covalently bound closed circular plasmid DNA by density centrifugation in a CsCl-gradient with ethidium bromide according to Bauer and Vinograd, Journal of Molecular Biology 33, 141–171, 1968. The DNA concentrations were determined in a fluorometer (model TKO 100 Hoefer Scientific Instruments, San Francisco) with the dye Hoechst 33258 according to the recommendations of the manufacturer.

Restriction Endonuclease Analysis (REA)

Portions of 0.75 µg purified, chromosomal DNA were digested separately at 37° C. for 4 h with 10 U HindIII, ClaI and EcoRI (Boehringer Mannheim). Gel electrophoresis was performed by using submerse horisontal agarose gel plates consisting of 150 ml 0.9% agarose (ultrapure DNA quality, BioRad Laboratories) and they were mulded as gel plates. 0.2 µg of a high molecular weight DNA marker (BRL) together with 0.5 µg of a DNA molecular weight marker VI (Boehringer Mannheim) were used as standards. In addition pHC 79, digested with EcoRI, was added to each well as an internal standard. Minimal band distorsion and maximal sharpness was reached by adding the DNA sample in a Ficoll loading buffer (2 g Ficoll, 8 ml water, 0.25% bromophenol).

Figure 2:
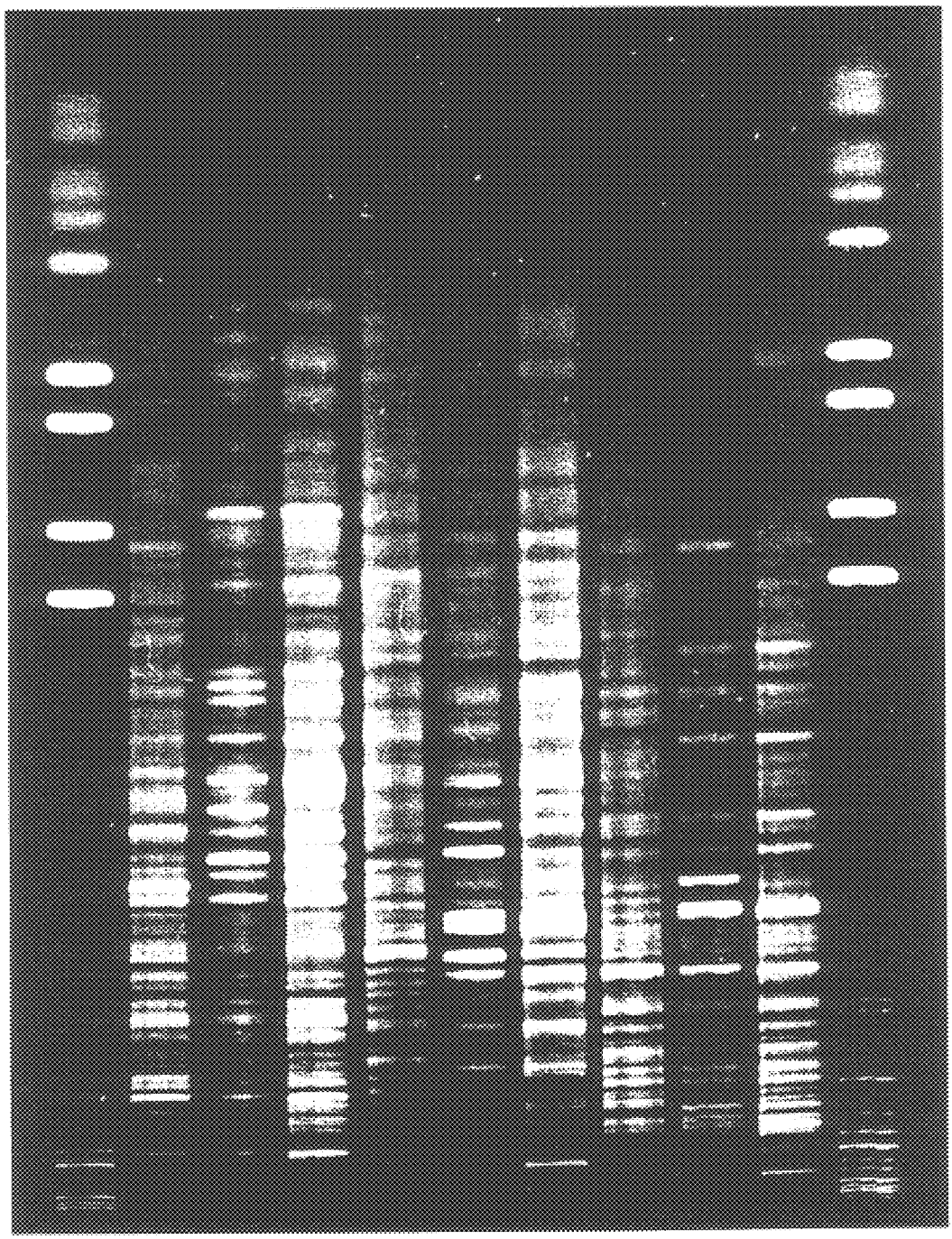
FIG. 2 shows a photography of an electrophoretic gel with strains which have been analysed by REA.

The fragments were separated on 0.9% agarose gels at 8.5° C. and 40 V for 18 h and were then stained for 20 min in ethidium bromide (2 µg/ml) and destained in distilled water and photographed. By this a well dispersed and fairly well separated bands were obtained down to a molecular weight of $1.2 \times 10^6$, see FIG. 2. This figure shows the REA pattern of the Lactobacillus plantarum strains JI:1, 299v and ATCC 149 $17^T$ (type strain) after sequential treatment with the restriction enzymes Ecco R1, Cla 1 and Hind III, respectively. The first and the last lane shows a marker. The strain AC:3 was analysed by REA and found to be rather different from the type strain of Lactobacillus salivarius ssp. salivarius (data not shown).

Examples of Feed Compositions

Preparation of Oatmeal Gruel in Industrial Scale

Oatmeal (318 kg), malted barley flour (12.8 kg) and water (1682 l) are mixed and heated to 88° C., the temperature being first maintained at 55° C. for 1 h and then at 88° C. for 0.5 h. The mixture was then cooled to 38° C. which requires about 0.5 h. At this temperature the starter culture Lactobacillus plantarum JI:1 is inoculated in an amount of 2 l to 2000 l of the mixture, giving a concentration of $2 \cdot 10^7$ CFU/ml. The whole is incubated at 38° C. for 15–20 h, after which pH should have been decreased to <3.9. The fermented mixture was then cooled to 6–8° C. and is after packaging and cool storage ready for distribution and sale.

The freshly prepared, final product contains $1-2 \cdot 10^9$ CFU/ml and after storage for 1–2 months the bacterial count has been reduced to about $5 \cdot 10^8$ CFU/ml.

The nutritional value of the above feed product is evident from the following table.

| Nutrition value | per 100 g | per 2 kg |
|---|---|---|
| Energy value | 240 kJ = 57 kcal | 4780 kJ = 1143 kcal |
| Protein | 2.1 g | 41.5 g |
| Dietary fibres* | 1.5 g | 29 g |
| Fat** | 1.1 g | 23 g |
| Carbohydrates | 10 g | 190 g |
| Vitamine B1 (thiamine) | 0.07 g | 1.3 g |

*according to ASP et al., J. Agric. Food Chem. 31:476–482
**according to SBR, Nordisk Metodikkomitté för livsmedel No. 131, 1989

By adding $CaCO_3$ in the above methods of preparation a feed composition having a higher bacterial count is obtained after a somewhat extended fermenting process (20–22 h).

By using Lactobacillus species AC:3 as a starter culture a corresponding oatmeal gruel is obtained.

Fermented Carrots

To prepare a batch of fermented carrots carrots (10 kg) are roughly grated or finely divided in any other way. Water (5 l) is boiled and then allowed to cool to 40° C., when Lactobacillus plantarum JI:1 (inoculant $2 \cdot 10^{11}$ CFU, corresponding to about 2 g freeze dried product or 20 ml freeze culture) and salt (100 g) are added. The grated carrots are layered with the inoculant fluid in a sterile container and densly packed. It is important that the vegetables are below the surface of liquid. The container is closed and then incubated at 24° C. for about 2 days. Ripening takes place in a refrigerator or cool larder for about 3–4 weeks. The fermented product can then be cool stored for about 1 year.

Freeze Dried Product
1 l water
200 g skim milk powder
2 g yeast extract
1 l bacterial suspension ($5 \cdot 10$ CFU/ml)

The above components are mixed and transferred to sterile plates which are placed on shelves in a freeze drier. The product is frozen to about −40° C. before the drying is started. After about 3 d the drying is finished and the product obtained is milled to a powder which is packed into sterile bags under a controlled nitrogene atmosphere. The keeping quality of the obtained product is about 2 years at freeze storage.

Freeze Culture 1 l of a bacterial suspension having a content of $5 \cdot 10^{10}$ CFU/ml is added to 1 l of a freeze medium having the following composition.

| | |
|---|---|
| potassium dihydrogenephosphate | 0.36 g |
| dipotassium hydrogenephosphate | 1.64 g |
| trisodium citrate | 1.18 g |
| magnesium sulphate | 0.5 g |
| glycerol | 240 g |
| distilled water | 760 ml |

The product obtained is frozen at −80° C. in 200 ml bottles.

Preparation of Ensilage

Ensilation is based on two principles, that is to lower the pH value of the green mass to 4.2 or lower and to exclude the air oxygen. 50 g of the freeze dried culture of Lactobacillus plantarum JI:1 is mixed with some litres of water to solve the powder and then additional water is added and a few kg of melasses to a total volume of 50 l. When the green mass is rolled into bales and enclosed into plastics then bacterial solution is dosed into the mass in an amount of about 1 l per 200 kg green mass by means of dosing pump mounted on the chaff cutter or the press. It is important to get a uniform admixture of the bacterial solution so that the added bacteria can grow in the whole of the bales. When ensilage is prepared in a silo the bacterial solution is added by means of a dosage pump through the fan of the silo.

Tests in Horses in Vivo

Administration of L. plantarum JI:1 in Oatmeal Gruel

This study comprises 10 trotters, five of which were given 2 l fermented oatmeal gruel each day for 8 weeks, while the other five horses which were not given oatmeal gruel took part in the study as reference horses. Samples of excrements were taken at six different times, directly before the horses were fed with the oatmeal gruel and then after 1, 3, 6 and 8 weeks and finally one week after that the horses had ceased to eat the oatmeal gruel. The microbiological analyses comprised the total number of lactobacilli, Enerobacteriaceae and Bacillus. The pH value of the excremental samples were also analysed. In addition the number of L. plantarum JI:1 of the total lactobacilli flora was analyzed.

In addition to the microbiological analysis also some subjective assessments of the status of the horses were done during the test period. This included consistency of the excrements, odour of the excrements, the fat of the horses, the gloss of the coat and finally the general condition of the horses.

The results show that the content of lactobacilli was substantially increased in two of the horses during the feed period. Both said horses had a low content of lactobacilli at the start of the test. From all horses which obtained the fermented oatmeal gruel the bacterium L. plantarum JI:1 was isolated from the excrements. The number varied from 1 to 72% of the total lactobacilli flora. Three of four horses had *L. plantarum* JI:1 in their excrements still one week after the completion of the feeding with the oatmeal gruel.

The number of Bacillus spp was decreased significantly in four of the horses during the feed period and one week after, while no change could be observed as to the number of Enterobacteriaceae or the pH values of the excrements during or after the test.

The fermented oatmeal gruel was much appreciated by the horses and became almost as "tit bit". There were also some signs indicating that the appetite of the horses was increased.

One of the horses, Luradej, registration number 90-4843, is noted for recurrent problems with the stomach and the intestines. Concurrently with the beginning of said problems the body temperature declines to about 36° C. After taking the fermented oatmeal gruel containing the bacteria *Lactobacillus plantarum* JI:1 for two weeks the temperature rose to a normal level of 37.5° C. for the first time in several months. When the horse ceased to eat the oatmeal gruel after having had it for 8 weeks the temperature again after 2–3 days decreased to about 36° C. After a short brake the horse was again fed with the oatmeal gruel which resulted in a temperature raise to the normal level. This was repeated once more at a later occasion. After two years daily intake of the described oatmeal gruel Luradej was given a bacterial concentrate of L. species AC:3 in the same amount. This resulted in an additional positive response in the general condition of the horse.

During the test period one of the horses was treated with a broad-spectrum antibiotic (Gentaject vet., 1.2 g twice a day for 7 days). When a horse is treated with this antibiotic there are normally some side effects, for instance problems with the stomach and the intestines for a long time. In this case the horse received the fermented oatmeal gruel during the whole antibiotic treatment and in addition during a number of weeks afterwards and the horse had no problems whatsoever neither with stomach nor intestines. This was repeated as a later occasion with another horse and another antibiotic giving the same positive results.

Colonizing of *L. plantarum* JI:1 and the Effect Thereof on the Content of Enterobacteriaceae, Bacillus. Clostridium in Horse Excrements The same product which has been described in the above test was used also in this study. In all 34 horses were included in the study. Twenty-six of them were located with six different trot trainers in the south of Sweden. The horses had different backgrounds, some of the horses had a problem with loose, malodorous excrements and/or poor fat and poor gloss of the hair coat. The horses were fed somewhat different as to, for instance, type of grain and certain supplementary feeds. Some of the horses also were periodically grazing.

The horses were fed with 2 l of fermented oatmeal feed per day for two months and in certain cases for three months. A small number of horses were periodically fed with only 1 l per day. This was for instance the case when some of the horses were grazing and then not so interested in eating anything else than grass. Samples of the excrements were taken directly before the horses were fed with the fermented feed and after having had said feed for 2–3 months. The microbiological analysis comprised the total number of lactobacilli, the number of *L. plantarum* JI:1 of the total number of lactobacilli, the total number of Enterobacteriaceae, Bacillus and Clostridium as well as the number of *B. cereus*.

In addition to the microbiological analysis some subjective assessments of the status of the horses were also done during the test period. This included consistency of the excrements, the odour of the excrements, fat, gloss of the coat, activity and appetite.

The results showed that the number of lactobacilli was significantly increased in the horses also in this study ($p<0.05$ after analysis by Wilcoxon signed ranks test). The median value before the start of the feeding was $1 \cdot 10^6$ cfu/g of excrements ($1 \cdot 10^5 - 1.7 \cdot 10^7$) and after 2–3 months of treatment $3.5 \cdot 10^6$ cfu/g ($1 \cdot 10^5 - 3.8 \cdot 10^7$). Preliminary *L. plantarum* JI:1 was found in the excrements from all horses after being fed.

The decrease in total number of Bacillus is very obvious ($p<0.001$ after analysis by Wilcoxon signed ranks test), with 80% of the analysed horses showing decreases in these counts after intake. Also sulphite-reducing clostridial counts were significantly decreased after treatment($p<0.05$ after analysis by Wilcoxon signed ranks test). Here 74% of the analysed horses had decreased amounts of clostridia (horses showing very low counts, less than $2 \cdot 10^2$ cfu/g of extrements, were omitted from the statistical analysis). As to the number of Enterobacteriaceae no tendency whatsoever could be observed.

Additional observations of interest which were made during this test were as follows:

Some of the horses had, at the start of the test, problems with diarrhea in stress situations and when warming up before a race. After having taken the fermented feed for a short time this problem ceased in all cases.

About 10 horses had problems with loose excrements at the beginning of the test. All horses obtained after some weeks at most, normal excrements.

Scarcely 10 horses had a problem with poor fat at the beginning of the project. All except one have after being fed with the fermented feed got a better fat.

About 5 horses had a poor gloss of the coat at the start of the test. They all got a finer coat after having taken the fermented feed for a couple of weeks.

Three horses have during the test period obtained antibiotics (two of the horses have obtained broad-spectrum antiobiotics and one a sulpha preparation). Not in any case has the antiobiotic had an adverse effect on the horses but the fermented oatmeal feed instead seems to have had a positive effect on the horses and compensated for the side effects which are otherwise common.

Two of the trainers had before the start of the test given sour milk to some of the horses without any noticeable result. Both were of the opinion that the effect was much better with the fermented oatmeal feed.

Three of the trainers had before the start of the test tested the product ColiCure on some of the horses with a poor result. All were of the opinion that the fermented feed gave a better result.

In a summing up of the effect of the fermented oatmeal feed on the 26 horses it has in 19 cases been observed a more or less positive effect on the intestinal flora of the horses and/or the common status of the horses. Only in 7 cases no evident positive effect has been observed. In a number of said cases there are explanations, for instance eating of concentrated feed of a bad hygienic quality or other problems which have for instance brought about medication of the horse.

Jaffa Qui, Example of Horse in Vivo

Jaffa Qui, registration number 92-1858, a very promising trotter, won her first race as an early three-year-old. When changing stable she was as a three-year-old for 6 months given water containing a considerable number of coli bacteria. When she was later moved to a new trainer it was gradually found that the whole stable had Rhino virus and Herpes virus. Jaffa Qui became the most ill of all the horses, probably owing to the reduced resistance caused by the bad water quality. She also got nettle rash and looked more miserable for every day. She did not cast her winter coat, became fluffy and almost stopped eating, and had no energy to training. After administration of the oatmeal gruel according to the invention, which she accepted at once and started to eat, she became better and better and it can now be declared that she has never before been so fine. She has a better fat than before and a glossing coat. She has also accepted training very well during the last months and has now qualified and made her debute.

Administration of Lactobacillus plantarum 299v to Horses with Gastritis

Five horses with gastritis problems, one of which had a partly cured gastritis after administration of Losec (Astra AB, Södertälje, Sweden), were treated with the oatmeal gruel described, for a number of weeks. All the horses showed full clinical recovery from the gastritis and two of the horses were 100% recovered by gastroscopy. In one case the horse was simultaneously treated with Losec. The details, as well as the results are given in the following Table.

TABLE

| Horse | Diagnosis before treatment | Dosage and duration of the treatment with L. plantarum JI:1 | Response to the treatment | Comments |
|---|---|---|---|---|
| Colombine | Gastritis | $2 \cdot 10^{12}$ cfu/d for 3 months | Full clinical recovery, 100% recovery by gastroscopy | No other medication |
| Fantasy Pride | Gastritis | $2 \cdot 10^{12}$ cfu/d for 1, 5 months | Full clinical recovery | No other medication |
| Faxa | Gastritis | $2 \cdot 10^{12}$ cfu/d for 1 month | Full clinical recovery | No other medication |
| Bali Pet | Gastritis | $2 \cdot 10^{12}$ cfu/d for 1 month | Full clinical recovery | 12 d treatment with Losec |
| Polk | Partly cured gastritis (60–70% recovery) | $2 \cdot 10^{12}$ cfu/d for 1 month | Full clinical recovery, 100% recovery by gastroscopy | No other medication |

The results show that the feed product of the invention has a potential of curing gastritis in horses.

Comparison Between Administration of L. Plantarum 299v and L. plantarum JI:1

During a short period the ten horses, who were included in the first test described above, were given fermented oatmeal gruel produced with L. plantarum 299v (isolated from human) which is part of the food ProViva® instead of with L. plantarum JI:1 (the horse strain). This was done without the knowledge of the trainer. After only one week he had realised that something was wrong with the oatmeal gruel. He had observed that the effect of the new supply of the fermented oatmeal gruel was less than before. Among other things the temperature of Luradej did not increase to slightly more than 37° C. as before in spite of the horse being fed with the fermented oatmeal gruel. This shows how important it is to use the right strain of the right lactobacillus and not only the right species of lactobacilli.

What is claimed is:

1. Equine feed product, comprising one or more strains of Lactobacillus selected from the group consisting of the strain Lactobacillus plantarum JI:1 DSM 11520, a variant having all the identifying characteristics thereof, the strain Lactobacillus species AC:3 DSM 12429, and a variant having all the identifying characteristics thereof.

2. Feed product according to claim 1, which has been fermented with said one or more strains.

3. Feed product according to claim 1, which is a cereal, vegetable, green forage or hay.

4. Feed product according to claim 2, which is a cereal, vegetable, green forage or hay.

5. Feed product according to claim 2, which is an oatmeal gruel fermented with said one or more strains.

6. Feed product according to claim 1, which is an ensilage.

7. Feed product according to claim 2, which is an ensilage.

8. Feed product according to claim 3, which is an ensilage.

9. Feed product according to claim 4, which is an ensilage.

10. A substantially pure strain of Lactobacillus plantarum JI:1 having the deposition number DSM 11520 or a variant thereof having all the identifying characteristics thereof.

11. A substantially pure strain of Lactobacillus species AC:3 having the deposition number DSM 12429 or a variant thereof having all the identifying characteristics thereof.

12. A method for prophylaxis or treatment of disturbances of equine intestinal flora comprising administering to an equine animal a medicament comprising an effective amount of the strain Lactobacillus plantarum JI:1 having the deposition number DSM 11520 or a variant having all the identifying characteristics thereof, or the strain Lactobacillus species AC:3 having the deposition number DSM 12429 or a variant having all the identifying characteristics thereof.

13. A method for prophylaxis or treatment of equine gastritis comprising administering to an equine animal a medicament comprising an effective amount of the strain Lactobacillus plantarum JI:1 having the deposition number DSM 11520 or a variant having all the identifying characteristics thereof, or the strain Lactobacillus species AC:3 having the deposition number DSM 12429 or a variant having all the identifying characteristics thereof.

14. A method for reducing the numbers of Bacillus ssp. and sulphite-reducing clostridia in equine intestines comprising administering to an equine animal a medicament comprising an effective amount of the strain Lactobacillus plantarum JI:1 having the deposition number DSM 11520 or a variant having all the identifying characteristics thereof, or the strain Lactobacillus species AC:3 having the deposition number DSM 12429 or a variant having all the identifying characteristics thereof.

* * * * *